United States Patent
Schwartz et al.

(10) Patent No.: US 7,156,816 B2
(45) Date of Patent: Jan. 2, 2007

(54) ULTRASOUND PULMONARY VEIN ISOLATION

(75) Inventors: Yitzhack Schwartz, Haifa (IL); Assaf Govari, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 179 days.

(21) Appl. No.: 10/304,500

(22) Filed: Nov. 26, 2002

(65) Prior Publication Data

US 2004/0102769 A1 May 27, 2004

(51) Int. Cl.
*A61B 17/20* (2006.01)
(52) U.S. Cl. ............................................. 601/2; 606/41
(58) Field of Classification Search ............ 606/32–52; 601/2
See application file for complete search history.

(56) References Cited

U.S. PATENT DOCUMENTS

| | | | |
|---|---|---|---|
| 4,401,124 A * | 8/1983 | Guess et al. ............... 600/458 |
| 4,979,948 A | 12/1990 | Geddes et al. |
| 5,092,336 A | 3/1992 | Fink |
| 5,109,859 A | 5/1992 | Jenkins |
| 5,242,438 A | 9/1993 | Saadatmanesh et al. |
| 5,366,490 A | 11/1994 | Edwards et al. |
| 5,391,199 A | 2/1995 | Ben-Haim |
| 5,433,708 A | 7/1995 | Nichols et al. |
| 5,590,657 A | 1/1997 | Cain et al. |
| 5,693,043 A | 12/1997 | Kittrell et al. |
| 5,807,395 A | 9/1998 | Mulier et al. |
| 5,840,025 A | 11/1998 | Ben-Haim |
| 5,891,134 A | 4/1999 | Goble et al. |
| 5,938,600 A | 8/1999 | Van Vaals et al. |
| 5,971,983 A | 10/1999 | Lesh |
| 6,004,269 A | 12/1999 | Crowley et al. |
| 6,012,457 A | 1/2000 | Lesh |
| 6,024,740 A | 2/2000 | Lesh et al. |
| 6,053,909 A | 4/2000 | Shadduck |
| 6,064,902 A | 5/2000 | Haissaguerre et al. |
| 6,090,084 A | 7/2000 | Hassett et al. |
| 6,117,101 A | 9/2000 | Diederich et al. |
| 6,156,028 A * | 12/2000 | Prescott ......................... 606/2 |
| 6,164,283 A | 12/2000 | Lesh |
| 6,190,382 B1 | 2/2001 | Ormsby et al. |
| 6,245,064 B1 | 6/2001 | Lesh et al. |
| 6,251,109 B1 | 6/2001 | Hassett et al. |
| 6,296,619 B1 * | 10/2001 | Brisken et al. ............... 604/22 |

(Continued)

FOREIGN PATENT DOCUMENTS

WO    WO 00/67656 A2    11/2000

(Continued)

OTHER PUBLICATIONS

European Search Report EP03257414 dated Apr. 5, 2004.

(Continued)

*Primary Examiner*—Michael Peffley
*Assistant Examiner*—Aaron Roane
(74) *Attorney, Agent, or Firm*—Louus J. Capezzuto

(57) ABSTRACT

A catheter introduction apparatus provides an ultrasound assembly for emission of ultrasound energy. In one application the catheter and the ultrasound assembly are introduced percutaneously, and transseptally advanced to the ostium of a pulmonary vein. An anchoring balloon is expanded to center an acoustic lens in the lumen of the pulmonary vein, such that energy is converged circumferentially onto the wall of the pulmonary vein when a transducer is energized. A circumferential ablation lesion is produced in the myocardial sleeve of the pulmonary vein, which effectively blocks electrical propagation between the pulmonary vein and the left atrium.

22 Claims, 4 Drawing Sheets

U.S. PATENT DOCUMENTS

| | | | |
|---|---|---|---|
| 6,490,474 B1 * | 12/2002 | Willis et al. | 600/424 |
| 6,529,756 B1 * | 3/2003 | Phan et al. | 600/374 |
| 6,632,223 B1 | 10/2003 | Keane | |
| 6,652,515 B1 * | 11/2003 | Maguire et al. | 606/41 |
| 6,679,269 B1 | 1/2004 | Swanson | |
| 6,689,128 B1 * | 2/2004 | Sliwa et al. | 606/41 |
| 6,740,040 B1 * | 5/2004 | Mandrusov et al. | 600/439 |
| 2001/0041880 A1 | 11/2001 | Brisken et al. | |
| 2002/0065512 A1 | 5/2002 | Fjield et al. | |
| 2003/0125726 A1 | 7/2003 | Maguire et al. | |

FOREIGN PATENT DOCUMENTS

| | | |
|---|---|---|
| WO | WO 01/72373 A2 | 10/2001 |
| WO | WO 01/82778 A2 | 11/2001 |

OTHER PUBLICATIONS

Pappone et al., Circumferential Radiofrequency Ablation of Pulmonary Vein Ostia: A New Anatomic Approach for Curing Atrial Fibrilation, Circulation 102;2619-2628 (2000).

Natale et al., First Human Experience with Pulmonary Vein Isolation Using a Through-the-Balloon Circumferential Ultrasound Ablation System for Recurrent Atrial Fibrillation, Circulation 102:1879-1882 (2000).

Scheinman et al., Nonpharmacological Approaches to Atrial fibrillation, Circulation 2001; 103:2120-2125.

Wang et al., Alternate Energy Sources for Catheter Ablation, Curr Cardiol Rep 1999 Jul.; 1(2):165-171.

Fried et al., Linear Lesions in Myocardium Created by Nd:YAG Laser Using Diffusing Optical Fibers: In Vitro and In Vivo results, Lasers Surg Med 2000;27(4):295-304.

Eigler et al., Implantation and Recovery of Temporary Metallic Stents in Canine Coronary Arteries, J Am Coll Cardiol 1993;22(4):1207-1213.

Middleton et al., Synthetic Biodegradable Polymers as Medical Devices, 1998.

Keane et al., Linear Atrial Ablation with a Diode Laser and Fiber Optic Catheter, Circulation 1999; 100:e59-e60.

Ware et al., Slow intramural Heating with Diffused Laser Light: A unique Method for Deep Myocardial Coagulation, Circulation; Mar. 30, 1999; pp. 1630-1636.

Christian Dorme et al. Ultrasonic Beam Steering Through Inhomogeneous Layers with a Time Reversal Mirror. IEEE Transactions on Ultrasonics, Ferroelectrics, and Frequency Control, vol. 43, No. 1, Jan. 1996.

M. Fink et al. Self Focusing in Inhomogeneous Media with "Time Reversal" Acoustic Mirrors. 1989 Ultrasonics Symposium—681.

Mathias Fink Time Reversal of Ultrasonic Fields—Part 1: Basic Principles. IEEE Transactions on Ultrasonics, Ferroelectrics, and Frequency Control, vol. 39, No. 5, Sep. 1992.

Mickaël Tanter et al. Focusing and Steering Through Absorbing and Aberrating Layers: Application to Ultrasonic Propagation Through the Skull, J. Acoust. Soc. Am 103 (5) Pt. 1, May 1998.

Mickaël Tanter et al. Focusing Through Skull with Time Reversal Mirrors. Application to Hyperthermia. 1996 IEEE Ultrasonics Symposium—1289.

Francois Wu et al. Time Reversal of Ultrasonic Fields—Part II: Experimental Results. IEEE Transactions on Ultrasonics, Ferroelectrics, and Frequency Control, vol. 39, No. 5, Sep. 1992.

European Search Report EP04250864 dated May 27, 2004.

* cited by examiner

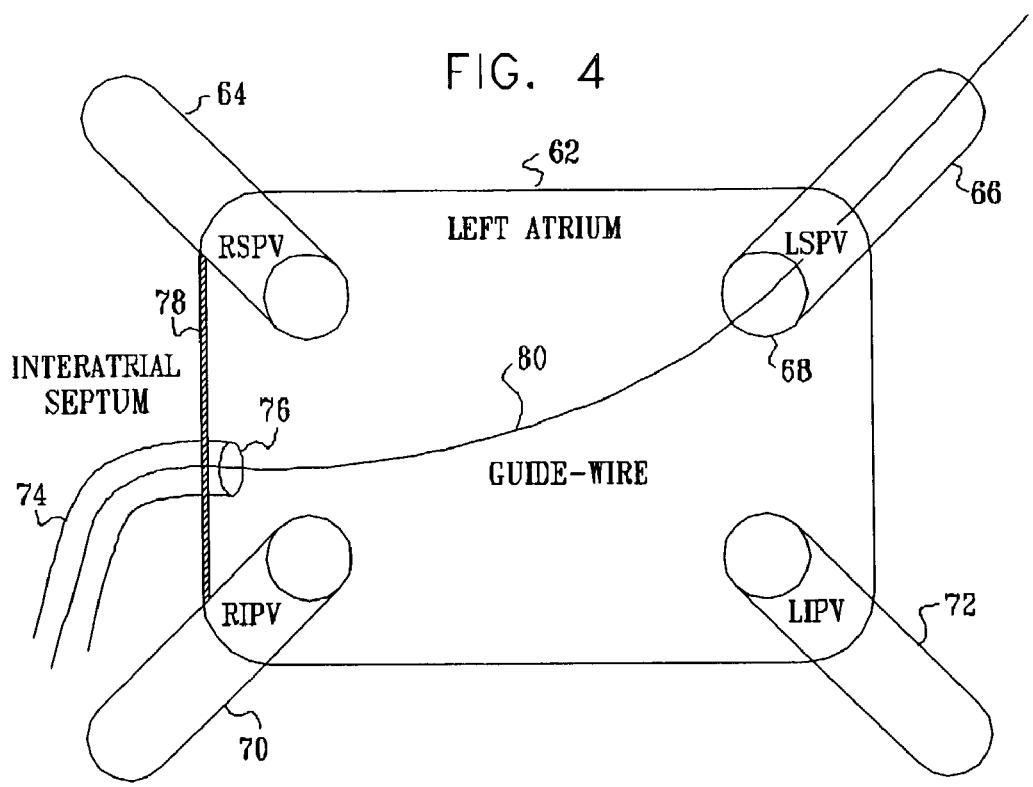
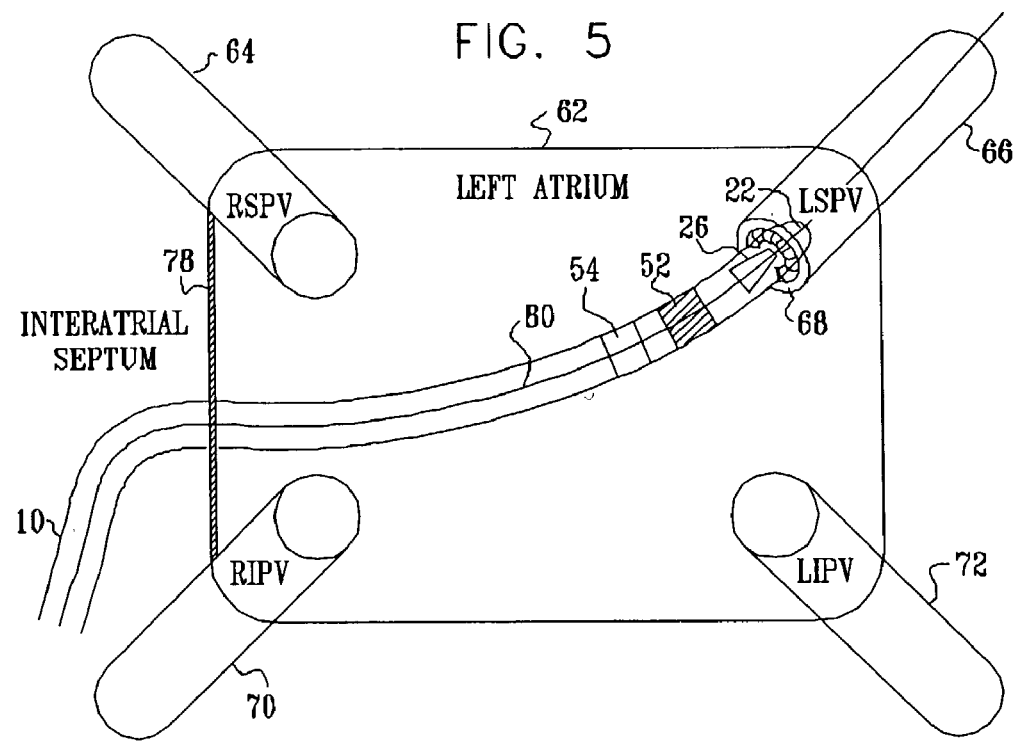

ULTRASOUND PULMONARY VEIN ISOLATION

BACKGROUND OF THE INVENTION

1. Field of the Invention

This invention relates to methods and apparatus for the medical treatment of disease of the heart. More particularly, this invention relates to a method and apparatus for treating cardiac arrhythmias by ablating in a vicinity of pulmonary venous tissue.

2. Description of the Related Art

Tissue ablation from the inner walls of hollow viscera of the body generally, and the vascular system in particular, has been found to be useful in the treatment of various medical conditions. Technological developments in intravascular catheters, manipulative instruments adapted to intravascular catheters, and catheter localization techniques have especially benefited the field of cardiology. Percutaneous transcatheter ablation has been used successfully in the treatment of conduction defects and arrhythmias of various types. Today, atrial tachyarrhythmias are a common application for ablative therapy.

Various ablative modalities have been employed in the past, such as ablation by direct heating. Energy can be conducted to the target tissue using various modalities, such as ultrasound, laser, resistive heating, and radiofrequency energy.

One ablative approach is the so-called "maze" technique. In general, the maze procedure attempts to block abnormal conduction patterns in the left atrium by establishing a maze-like pattern of linear lesions in the left atrial wall.

Atrial arrhythmias are known to be associated with abnormal electrical activity of tissue foci in the vicinity of the pulmonary veins, especially the superior pulmonary veins. Various ablative treatments of such foci have been attempted. For example, the production of linear atrial lesions by radiofrequency ablation, in combination with ablation of suspected arrhythmogenic foci has been performed using transcatheter techniques.

More recently, circumferential lesions at or near the ostia of the pulmonary veins have been created to treat atrial arrhythmias. U.S. Pat. Nos. 6,012,457 and 6,024,740, both to Lesh, disclose a radially expandable ablation device, which includes a radiofrequency electrode. Using this device, it is proposed to deliver radiofrequency energy to the pulmonary veins in order to establish a circumferential conduction block, thereby electrically isolating the pulmonary veins from the left atrium.

Radiofrequency ablation using multiple contiguous circumferential points, guided by electro-anatomical mapping is proposed in the document, *Circumferential Radiofrequency Ablation of Pulmonary Vein Ostia: A New Anatomic Approach for Curing Atrial Fibrillation,* Pappone C, Rosanio S, Oreto G, Tocchi M, Gugliotta F, Vicedomini G, Salvati A, Dicandia C, Mazzone P, Santinelli V, Gulletta S, Chierchia S, Circulation 102:2619–2628 (2000). It is emphasized that particular care must be exercised to ensure that the ablation sites are indeed contiguous; otherwise irregular electrical activity in the pulmonary vein may continue to contribute to atrial arrhythmia.

It has also been proposed to produce circumferential ablative lesions using ultrasound energy delivered via a cylindrical ultrasound transducer through a saline-filled balloon. This technique is described in the document, *First Human Experience With Pulmonary Vein Isolation Using a Through-the-Balloon Circumferential Ultrasound Ablation System for Recurrent Atrial Fibrillation,* Natale A, Pisano E, Shewchik J, Bash D, Fanelli R, M D; Potenza D; Santarelli P; Schweikert R; White R; Saliba W; Kanagaratnam L; Tchou P; Lesh M, Circulation 102:1879–1882 (2000). Ablation times on the order of 2 minutes are reported.

U.S. Pat. No. 6,117,101 to Diederich et al. discloses a technique for producing circumferential lesions for electrical isolation of the pulmonary veins. Using a balloon catheter, a cylindrical ultrasound transducer is provided on an inner member within a balloon, and emits a radial ultrasound signal that is sonically coupled to the balloon's outer skin.

A known drawback in the use of ultrasound energy for cardiac tissue ablation is the difficulty in controlling the local heating of tissue. There are tradeoffs between the clinical desire to create a sufficiently large lesion to effectively ablate an abnormal tissue focus, or block an aberrant conduction pattern, and the undesirable effects of excessive local heating. If the ultrasound device creates too small a lesion, then the medical procedure could be less effective, or could require too much time. On the other hand, if tissues are heated excessively then there could be local charring effects due to overheating. Such overheated areas can develop high impedance, and may form a functional barrier to the passage of heat. The use of slower heating provides better control of the ablation, but unduly prolongs the procedure.

In consideration of these, and other factors, it is appropriate, in designing a practical ultrasound emitter, to consider the amplitude of the ultrasound signal, the amount of time required for the energy application, the size of the electrode, and the contact area, as well as ease of positioning, withdrawal, and repositioning of the device so as to be able to conveniently produce multiple lesions during the same medical procedure.

Previous approaches to controlling local heating include the inclusion of thermocouples within the electrode and feedback control, signal modulation, local cooling of the catheter tip, and fluid assisted techniques, for example perfusion of the target tissue during the energy application, using chilled fluids. Typical of the last approach is described by Mulier et al. in U.S. Pat. No. 5,807,395.

Publications which describe various medical techniques of interest include:

Scheinman M M, Morady F. Nonpharmacological Approaches to Atrial Fibrillation. *Circulation* 2001;103: 2120–2125.

Wang P J, Homoud M K, Link M S, Estes III N A. Alternate Energy Sources for Catheter Ablation. *Curr Cardiol Rep* 1999 July; 1(2):165–171.

Fried N M, Lardo A C, Berger R D, Calkins H, Halperin H R. Linear Lesions in Myocardium Created By Nd:YAG Laser Using Diffusing Optical Fibers: In Vitro and In Vivo Results. *Lasers Surg Med* 2000;27(4):295–304.

Eigler N L, Khorsandi M J, Forrester J S, Fishbein M C, Litvack F. Implantation and Recovery of Temporary Metallic Stents in Canine Coronary Arteries. *J Am Coll Cardiol* 1993; 22(4):1207–1213.

Synthetic Biodegradable Polymers as Medical Devices; by John C. Middleton and Arthur J. Tipton. 1998.

Keane D, Ruskin J, Linear Atrial Ablation With A Diode Laser And Fiber Optic Catheter. *Circulation* 1999; 100: e59–e60.

Ware D, et al., Slow intramural heating with diffused laser light: A unique method for deep myocardial coagulation. *Circulation*; Mar. 30, 1999; pp. 1630–1636.

Other medical technologies of interest are described in U.S. Pat. No. 5,891,134 to Goble et al., U.S. Pat. No.

5,433,708 to Nichols et al., U.S. Pat. No. 4,979,948 to Geddes et al., U.S. Pat. No. 6,004,269 to Crowley et al., U.S. Pat. No. 5,366,490 to Edwards et al., U.S. Pat. Nos. 5,971,983, 6,164,283, and U.S. Pat. No. 6,245,064 to Lesh, U.S. Pat. No. 6,190,382 to Ormsby et al., U.S. Pat. Nos. 6,251,109 and 6,090,084 to Hassett et al., U.S. Pat. No. 5,938,600 to Swartz et al., and U.S. Pat. No. 6,064,902 to Haissaguerre et al.

All of the patents and publications cited in this disclosure are incorporated herein by reference.

SUMMARY OF THE INVENTION

It is therefore a primary object of some aspects of the present invention to provide improved apparatus and method for electrically isolating the pulmonary vein by accomplishing a circumferential conduction block surrounding the pulmonary vein ostium in complishing a circumferential conduction block surrounding the pulmonary vein ostium in a single ablation application of ultrasound energy.

It is another object of some aspects of the present invention to reduce the time required to perform ultrasonic isolation of the pulmonary veins.

These and other objects of the present invention are attained by a catheter introduction apparatus that includes an ultrasound assembly for emission of ultrasound energy. In one application, the catheter and the ultrasound assembly are introduced percutaneously, and transseptally advanced to the ostium of a pulmonary vein. An anchor such as an anchoring balloon is expanded to center an acoustic lens in the lumen of the pulmonary vein, such that energy is converged circumferentially onto the wall of the pulmonary vein when a transducer is energized. A circumferential ablation lesion is produced in the myocardial sleeve of the pulmonary vein, which effectively blocks electrical propagation between the pulmonary vein and the left atrium.

There is therefore provided, in accordance with an embodiment of the present invention, a method for electrically isolating a left atrium of a heart from a pulmonary vein, including the steps of:

introducing an ultrasound assembly into said heart proximate an ostium of said pulmonary vein;

anchoring said ultrasound assembly to said pulmonary vein using an anchor; and thereafter conducting ultrasound energy in a path extending from said ultrasound assembly to a circumferential ablation region of said pulmonary vein, said path substantially avoiding said anchor.

In an embodiment, said step of conducting said ultrasound energy is performed by converging said ultrasound energy into a circumferential line of focus that intersects said ablation region.

In an embodiment, said anchor includes a balloon, and said step of aligning is performed by expanding said balloon to engage said pulmonary vein.

In an embodiment, said step of conducting said ultrasound energy is performed in exactly one application.

In an embodiment, a duration of said one application is less than 300 seconds.

In an embodiment, said step of introducing is performed by:

disposing said ultrasound assembly on an intravascular catheter; and passing a distal portion of said intravascular catheter through a blood vessel into said heart, wherein said ultrasound assembly is spaced apart from said ablation region, wherein said path has a generally forward direction from said ultrasound assembly toward said ablation region.

In this case, in an embodiment, said step of passing said distal portion of said intravascular catheter includes activating said ultrasound assembly to apply ultrasound energy to a fossa ovalis of said heart.

In an embodiment, the method includes the step of adjusting a beam of said ultrasound energy to conform to an anatomy of said ablation region.

In an embodiment, the method includes the step of conducting an effective amount of energy from said ultrasound assembly to ablate a portion of a fossa ovalis of said heart while performing said step of introducing said ultrasound assembly.

There is further provided, in accordance with an embodiment of the present invention, an apparatus for electrically isolating a cardiac chamber, including:

an intravascular catheter having a distal end; an anchor proximate said distal end; and an ultrasound transducer assembly disposed external to said anchor for emitting ultrasound energy that is directed to a circumferential ablation region, a path of said ultrasound energy substantially avoiding said anchor.

In an embodiment, the apparatus includes a sensor disposed in said catheter for detecting cardiac electrical activity. For some application, the apparatus includes a transmitting antenna disposed in said catheter for transmitting signals from said sensor.

In an embodiment, said anchor includes a balloon.

In an embodiment, a body section of said ultrasound transducer assembly has a proximal cross section and a distal cross section, said proximal cross section being larger than said distal cross section. For some applications, said body section is a truncated cone, and an inclination angle of said truncated cone is about 20 degrees.

In an embodiment, said ultrasound transducer assembly includes an omnidirectional lens that focuses a beam of said ultrasound energy circumferentially on said ablation region. For some applications, said ultrasound transducer assembly includes an array of transducer elements, and a control unit for controlling individual ones of said transducer elements to shape said beam.

In an embodiment, in an operational position said ultrasound transducer assembly is spaced apart from said ablation region.

In an embodiment, said ultrasound transducer assembly operates at a frequency of between about 3 and 4 MHz.

In an embodiment, said ultrasound transducer assembly includes:

a diffraction grating for directing said ultrasound energy that is output from said ultrasound transducer assembly in a desired direction; and a transducer layer capable of transducing energy delivered thereto at different frequencies, said transducer layer being disposed within said catheter proximate said diffraction grating.

In this case, in an embodiment, said diffraction grating is a thin-film disposed on an external surface of said catheter.

In an embodiment, said ultrasound transducer assembly has a bandwidth that is between about 50% and about 80% of a primary operating frequency thereof.

There is yet further provided, in accordance with an embodiment of the present invention, an apparatus for electrically isolating a cardiac chamber, including:

an intravascular catheter;

an anchor disposed proximate a distal end of said catheter; and an ultrasound transducer assembly disposed proximal to said anchor for emitting ultrasound energy, a path of said ultrasound energy substantially avoiding said anchor, wherein a body section of said ultrasound transducer assembly has a proximal cross sectional area and a distal cross sectional area, said proximal cross sectional area being larger than said distal cross sectional area, and wherein said ultrasound transducer assembly emits said ultrasound energy as a beam that is focused on an ablation region that substantially surrounds said ultrasound transducer assembly.

In an embodiment, the apparatus includes a sensor disposed in said catheter for detecting cardiac electrical activity. In this case, in an embodiment, the apparatus includes a transmitting antenna disposed in said catheter for transmitting signals from said sensor.

In an embodiment, said anchor includes a balloon.

In an embodiment, said body section is a truncated cone, and an inclination angle of said truncated cone is about 20 degrees.

In an embodiment, said ultrasound transducer assembly includes an array of transducer elements, and a control unit for controlling individual ones of said transducer elements to shape said beam.

In an embodiment, in an operational position said ultrasound transducer assembly is spaced apart from said ablation region.

In an embodiment, said ultrasound transducer assembly operates at a frequency of between about 3 and 4 MHz.

In an embodiment, said ultrasound transducer assembly includes:
 a diffraction grating for directing said ultrasound energy that is output from said ultrasound transducer assembly in a desired direction; and
 a transducer layer capable of transducing energy delivered thereto at different frequencies, said transducer layer being disposed within said catheter proximate said diffraction grating.

In an embodiment, said diffraction grating is a thin-film disposed on an external surface of said catheter.

In an embodiment, said ultrasound transducer assembly has a bandwidth that is between about 50% and about 80% of a primary operating frequency thereof.

BRIEF DESCRIPTION OF THE DRAWINGS

For a better understanding of these and other objects of the present invention, reference is made to the detailed description of the invention, by way of example, which is to be read in conjunction with the following drawings, wherein:

FIGS. 4 and 5 schematically illustrates certain aspects of a method of intracardiac catheter access during a first phase of the method shown in FIG. 3.

DESCRIPTION OF THE PREFERRED EMBODIMENT

In the following description, numerous specific details are set forth in order to provide a thorough understanding of the present invention. It will be apparent to one skilled in the art, however, that the present invention may be practiced without these specific details. In other instances, well known circuits, control logic, and other apparatus have not been shown in detail in order not to unnecessarily obscure the present invention.

Figure 1:
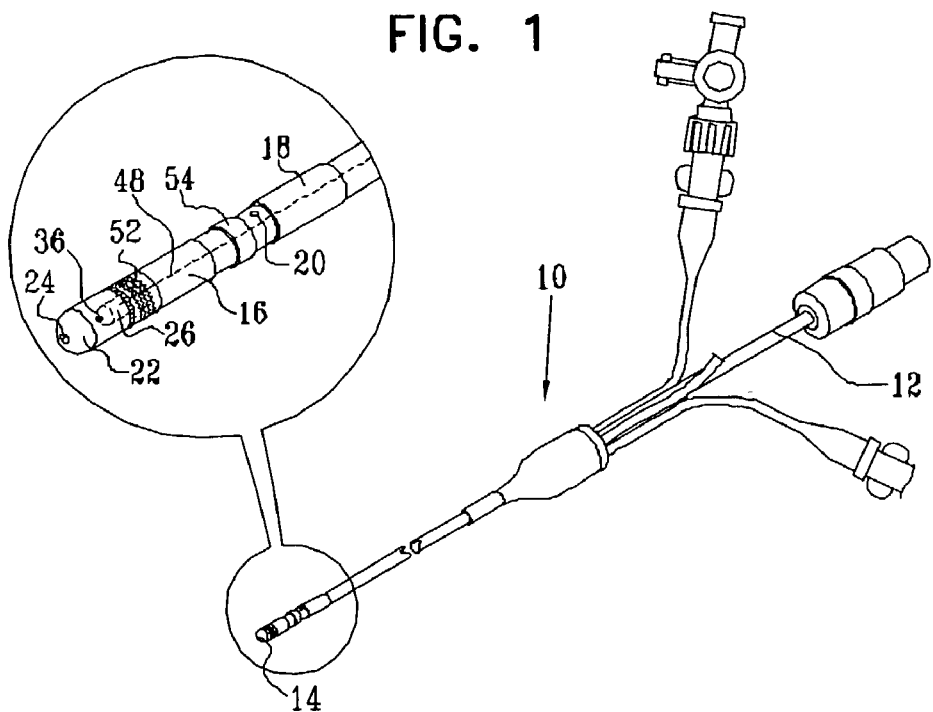
FIG. 1 is a perspective view of a therapeutic catheter that is constructed and operative in accordance with a preferred embodiment of the invention.

Turning now to the drawings, reference is made to FIG. 1, which illustrates a medical device that is constructed and operative in accordance with a preferred embodiment of the invention. An intravascular catheter 10 has a proximal end 12 and a distal end 14. The distal end 14 is provided with at least one seal 16, and optionally a second seal 18. The seals 16, 18 are preferably inflatable balloons, made from rubber, polyurethane, or a similar elastic material. The catheter 10 has one or more lumens, which conduct fluid for inflating and deflating the seals 16, 18. One of the lumens terminates in a port 20, and is useful for injection of fluids and withdrawal of blood as may be required during use. Other lumens are provided for passage of guidewires and instruments therethrough. An inflatable anchoring balloon 22, shown in a deflated condition, is located distal to the seals 16, 18. The catheter 10 also has a coaxial guidewire lumen 24. Disposed near the tip of the catheter 10, approximately 1 cm proximal to the anchoring balloon 22, is an ultrasound transducer assembly 26 which is coaxial with the catheter 10.

Figure 2:
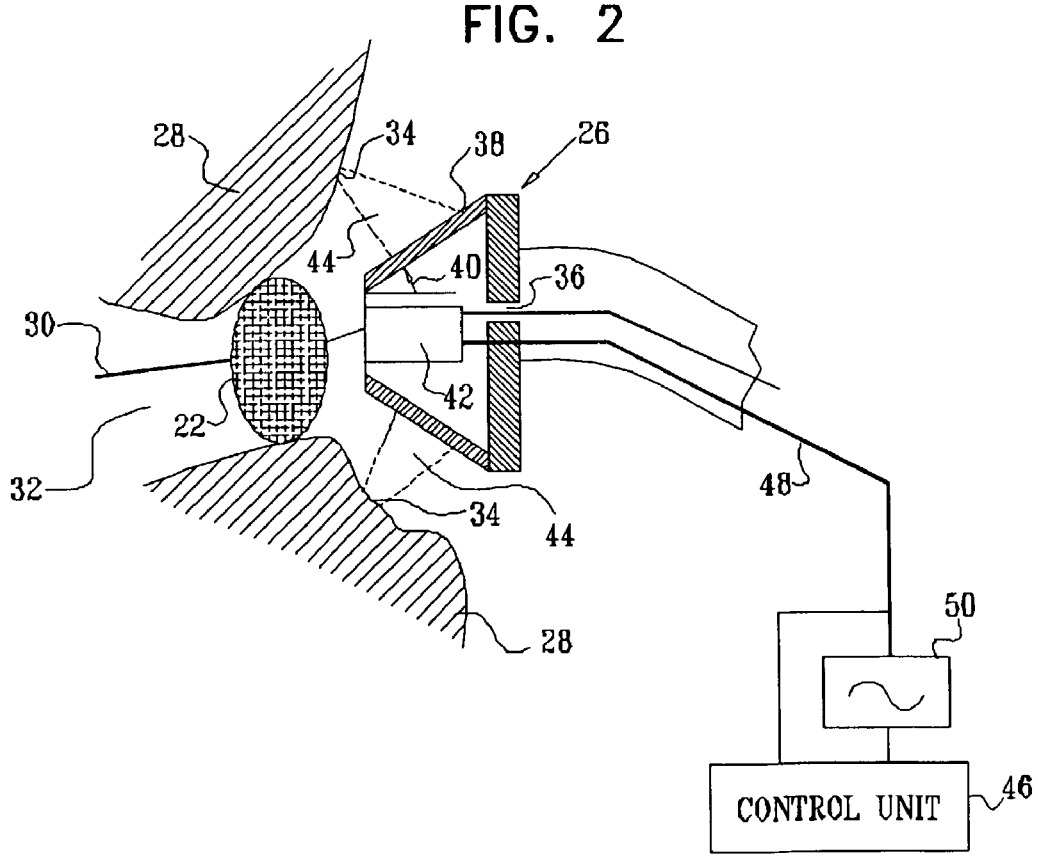
FIG. 2 is a sectional schematic view of a transducer assembly in an operational position at a pulmonary vein ostium in accordance with a preferred embodiment of the invention.

Reference is now made to FIG. 2, which is a sectional schematic view of the transducer assembly 26 in an operational position at a pulmonary vein ostium 28 in accordance with a preferred embodiment of the invention. The disclosure of FIG. 2 should be read in conjunction with FIG. 1. The catheter 10 has been slidably inserted over a guidewire 30 (through guidewire lumen 24), which was previously introduced into a pulmonary vein lumen 32. The anchoring balloon 22 is expanded and fixes the apparatus in position. The transducer assembly 26 is disposed proximate the ostium 28, external to the anchoring balloon 22. It will be noted that the transducer assembly 26 is not in direct contact with either the anchoring balloon 22, nor with target tissue 34 to be ablated, which is located near the ostium 28. Advantageously, the placement of the transducer assembly 26 outside the anchoring balloon 22 allows for simplicity of construction, and for direct application of ultrasound energy to the target tissue 34, thereby avoiding distortion and loss of precision in energy delivery that might occur if the energy passed through the wall of the balloon. Moreover, as is further disclosed hereinbelow, the use of ultrasonic beam focusing techniques eliminates the difficulty of physically conforming the transducer to the wall of the pulmonary vein, as is required by conventional techniques, which often required multiple versions of the catheter 10, each dimensioned to one of many anatomic variations of the structures near the target ablation zone. Since direct contact between the transducer assembly 26 and the target tissue 34 is eliminated according to this embodiment of the present invention, it is also not required that the transducer assembly 26 vary sectionally in stiffness, a requirement which was disclosed, for example, in the above-noted U.S. Pat. No.

6,117,101. Variation in stiffness was required in order to assure stable engagement with the pulmonary vein.

The transducer assembly 26 has a lumen 36 for passage therethrough of the guidewire 30. A body section 38 is preferably shaped as a truncated cone, preferably having an inclination angle 40 of approximately 20 degrees. Thus, the cross section of a proximal portion of the body section 38 is larger than the cross section of its distal portion. A piezoelectric element 42 of known type, such as a ceramic, is present within the body section 38. The transducer assembly 26 functions as an omnidirectional ultrasonic lens, forming a generally forward-directed circumferential beam 44, indicated by dashed lines in FIG. 2. The beam 44 converges onto the target tissue 34. The piezoelectric element 42 may be realized as an array of transducers, which can be tuned, under control of a control unit 46, so as to shape the beam 44 as may be required for a particular ablation procedure, in order to adapt the beam to the local anatomy. This can be done in a known manner, for example by operating elements of the array out of phase with one another. The transducer assembly 26 is connected by a cable 48 to a suitable power source 50 and to the control unit 46.

Preferably the transducer assembly 26 is 4.0 mm in length, and has an OD of 2.6 mm. The transducer assembly 26 is quarter-wave impedance matched, using air-backing material within the body section 38. It preferably operates at an excitation frequency of 3–4 MHz, and has a focal depth of 15 mm. Typical driving power is 30–40W.

Structures suitable for the components of the transducer assembly 26 are disclosed, for example, in U.S. Pat. No. 6,296,619, and the above-noted U.S. Pat. No. 6,117,101, which are incorporated herein by reference. It is also possible to construct the transducer assembly 26 as a thin-film polymer wrapped about the outer surface of the catheter 10.

Preferably, the active sites to be ablated are identified using the location and mapping system disclosed in commonly assigned U.S. Pat. No. 5,840,025, which is herein incorporated by reference. Certain components of the location and mapping system are incorporated into the distal end 14 of the catheter 10, namely a sensor 52, which is a mapping electrode, and a transmitting antenna 54, which can be a dipole antenna. The sensor 52 detects local electrical activity of the heart, and the antenna 54 transmits signals to a plurality of receiving antennae (not shown) which are placed on the body surface of a patient during use. The distal end 14 can be radio-opaque, in order to facilitate its localization by conventional radiographic techniques, alternatively or in addition to the system disclosed in the above-noted U.S. Pat. No. 5,840,025.

In embodiments in which the system disclosed in the above-noted U.S. Pat. No. 5,840,025 is not used, the sensor 52 performs conventional monitoring of local electrical activity, and the antenna 54 can then be omitted.

Figure 3:
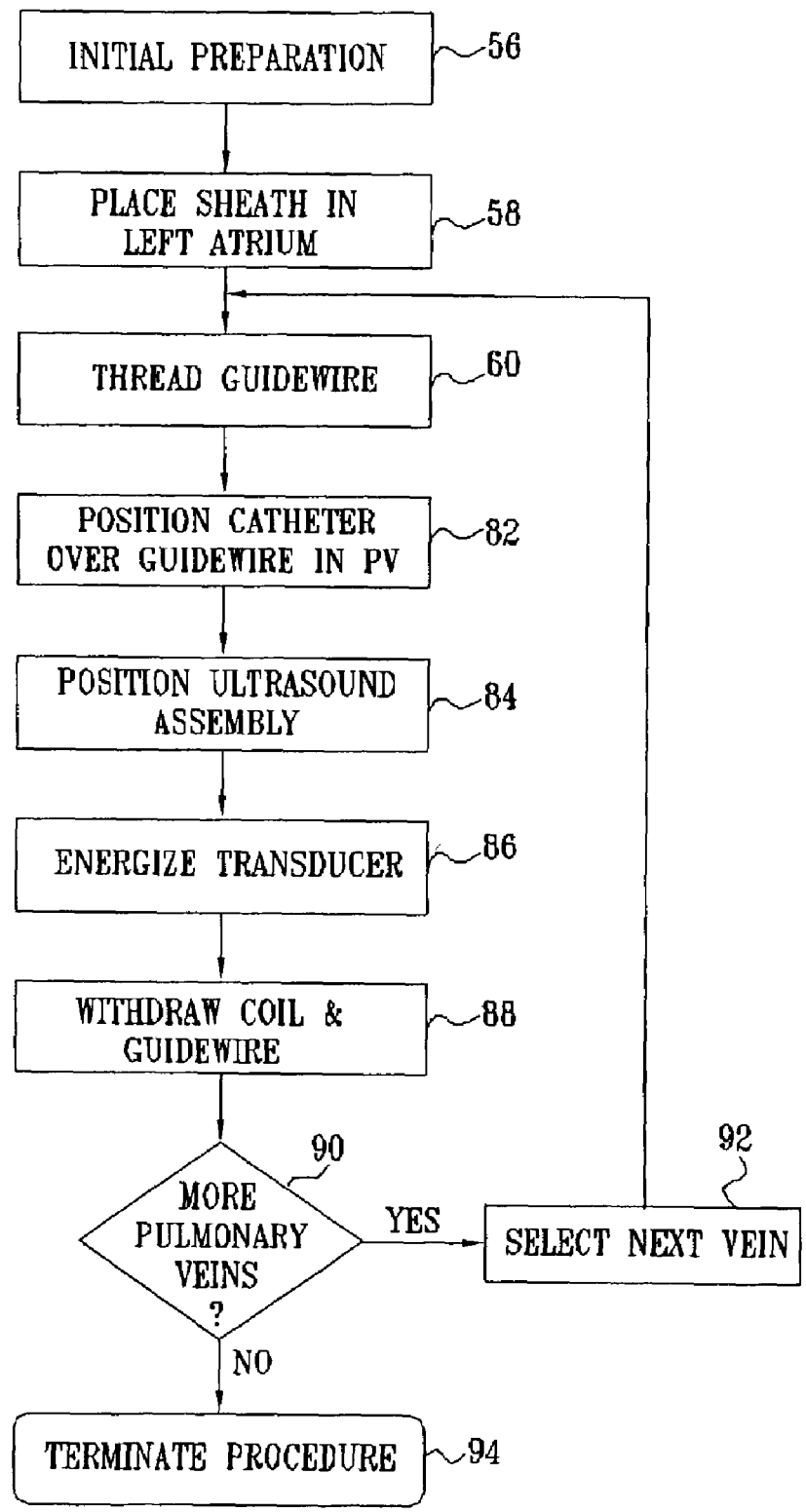
FIG. 3 is a flow chart of a method for electrically isolating pulmonary veins, which is operative in accordance with a preferred embodiment of the invention.

Reference is now made to FIG. 3, which is a flow chart of a method for electrically isolating pulmonary veins, which is operative in accordance with a preferred embodiment of the invention. The description of FIG. 3 should be read in conjunction with FIG. 1.

In initial step 56, routine preparation of a subject (not shown) and equipment are accomplished. This includes attachment of various monitoring and grounding leads, as may be required for electrophysiological monitoring of the procedure, and for the operation of the above-noted location and mapping system.

Next, at step 58, a series of events begins, ultimately leading to the positioning of the catheter 10 and the transducer assembly 26 at the ostium of a pulmonary vein. Step 58 is conventional. In a preferred approach, the venous system is accessed using the well-known Seldinger technique, in which an introducer sheath is positioned in a peripheral vein, typically a femoral vein. A guiding sheath is introduced through the introducer sheath, and is advanced via the inferior vena cava into the right atrium. Then, using a Brockenbrough needle, the fossa ovalis of the interatrial septum is punctured, and the puncture dilated if necessary. The Brockenbrough needle is withdrawn, and the guiding sheath placed in the left atrium. Alternatively, the ablation catheter is energized as it contacts the interatrial septum, usually at the fossa ovalis, in order to facilitate passage through the septum. Ablation of septal tissue eases the passage of the catheter through the septum, reduces the amount of hardware used, and shortens the procedure, as it is not necessary to pass a dilator through the fossa ovalis. It is also possible to access the left atrium via the superior vena cava, or to use a retrograde intra-arterial technique.

Next, in step 60 a guidewire is advanced through the guiding sheath, through the left atrial chamber, and into a pulmonary vein.

The order in which the specific pulmonary veins are visited and treated is arbitrary, but it is preferable to concentrate first on the two superior pulmonary veins, in which the muscular sleeves are more prominent than in the inferior pulmonary veins. Thereafter the inferior pulmonary veins may be isolated. Typically, an ablation procedure involves the isolation of all four pulmonary veins.

Reference is now made to FIG. 4, which schematically illustrates certain aspects of the method of electrical pulmonary vein isolation in accordance with a preferred embodiment of the invention. The description of FIG. 4 should be read in conjunction with FIG. 3. FIG. 4 represents the status at the completion of step 60 (FIG. 3). A cutaway view of a left atrial chamber 62 includes a right superior pulmonary vein 64 and a left superior pulmonary vein 66, whose ostium 68 is indicated. The view of FIG. 4 also includes a right inferior pulmonary vein 70, and a left inferior pulmonary vein 72. A conventional guiding sheath 74 has a distal end 76 which has been positioned on the left atrial side of an interatrial septum 78. A conventional guidewire 80 extends through the lumen of the guiding sheath 74, into the lumen of the left superior pulmonary vein 66. It will be understood that while the guidewire 80 is shown in relation to the left superior pulmonary vein 66, the technique is equally applicable to the other pulmonary veins.

Referring again to FIG. 3, at step 82, the guiding sheath is withdrawn, and an ablation catheter is slidably tracked over the guidewire, using the guidewire lumen of the catheter. The catheter is advanced into the left atrium. While maneuvering the catheter in the heart, its position is preferably monitored by the location and mapping system disclosed in the above-noted U.S. Pat. No. 5,840,025, or alternatively by conventional imaging modalities. The tip of the catheter is located at the ostium of a pulmonary vein.

Reference is now made to FIG. 5, which schematically illustrates certain aspects of the method of electrical pulmonary vein isolation in accordance with a preferred embodiment of the invention. The description of FIG. 5 should be read in conjunction with FIGS. 3 and 4. FIG. 5 represents the status at the completion of step 82 (FIG. 3). Structures in FIG. 5 which are identical to corresponding structures in FIG. 4 have been given like reference numerals. The shaft of the catheter 10 extends through the interatrial septum 78. The anchoring balloon 22 and the transducer assembly 26 lie across the ostium 68 of the left superior pulmonary vein 66, and the principal axis of the transducer assembly 26 is substantially coaxial with the left superior pulmonary vein 66. During placement, the anchoring balloon 22 is deflated.

Referring again to FIG. 3, at step 84 the transducer assembly 26 is positioned such that when it is energized, the circumferential focus of the ultrasound beam intersects the pulmonary vein in which the target tissue is located. Positioning is preferably accomplished by inflating the anchoring balloon 22 so that it expands to fill the lumen of the ostium 68. The anchoring balloon 22 is then in circumferential contact with the intima of the pulmonary vein. The distal end 14 of the catheter 10 and the transducer assembly 26 are thus forced into a central position with respect to the lumen of the ostium 68. Perfusion through one of the catheter ports may be employed during step 84 to minimize stasis of blood in the region.

In step 86, once the position of the transducer assembly 26 is confirmed, the transducer assembly 26 is energized, and ultrasound energy converges in a circumferential pattern to the target tissue. Local heating caused by absorption of the ultrasound energy results in ablation of the target tissue. The path taken by the ultrasound energy extends directly from the transducer assembly 26 to the target tissue, and does not pass through the anchoring balloon 22.

Referring again to FIG. 3, the transfer of ultrasound energy from the transducer assembly 26 to the pulmonary vein in step 86 occurs in a single, relatively short application. The energy application is preferably controlled in response to continuous electrophysiological monitoring, an end point being reached when conduction block is confirmed across the line of ablation. For some applications, feedback techniques known in the art, e.g., on-site temperature measurements, are used to regulate the application of energy to the tissue.

Upon completion of the ablation, in step 88 the anchoring balloon 22 is deflated. The distal end 14 of the catheter 10 is withdrawn into the left atrial chamber. The guidewire 80 is also withdrawn from the pulmonary vein.

Next, at decision step 90, a test is made to determine if more pulmonary veins remain to be electrically isolated. If the determination is affirmative then control proceeds to step 92, where the next pulmonary vein is selected. Control then returns to step 60.

If the determination at decision step 90 is negative, then control proceeds to final step 94. The anchoring balloon is deflated, and the entire apparatus withdrawn from the patient. The procedure thereupon terminates.

Figure 6:
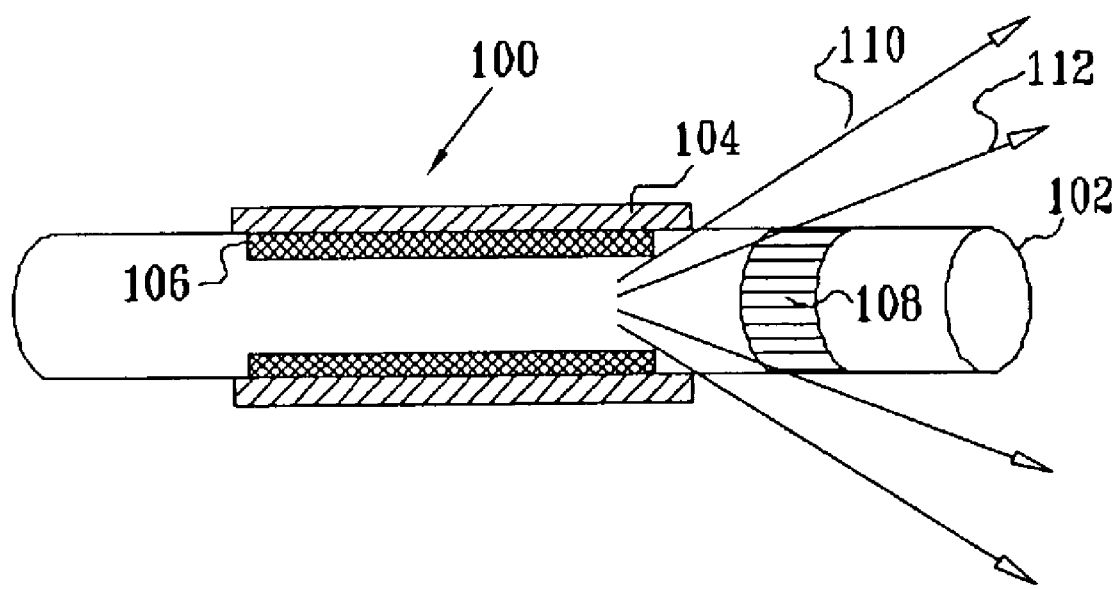
FIG. 6 schematically illustrates a transducer assembly, in accordance with a preferred embodiment of the present invention.

Reference is now made to FIG. 6, which schematically illustrates a transducer assembly 100 that is constructed and operative in accordance with an alternate embodiment of the invention. The transducer assembly 100 is incorporated in a segment of a catheter shaft 102. A diffraction grating lens 104 is formed as a thin-film layer on the outside of the catheter shaft 102, using known techniques. The catheter shaft 102 is sonolucent, at least in the segment occupied by the transducer assembly 100. A wide band ultrasound transducer 106 opposes the diffraction grating lens 104 within the catheter shaft 102. A sensor 108 positioned near the transducer assembly 100 has the same function as the sensor 52 (FIG. 1).

The diffraction grating lens 104 enables control over the direction of the ultrasound beam that is emitted from the transducer assembly 100. By appropriately changing the frequency of the ultrasound generator, the ultrasound beam can be steered in various directions, as indicated by two representative directions 110, 112.

For example, an ultrasound transducer having a bandwidth that is 50% of its primary operating frequency of 8 MHz can vary the diffraction angle by more than 60 degrees as the output beam frequency varies over the operating bandwidth.

The embodiment of FIG. 6 has the advantage of a low profile, which does not interfere with its introduction into the pulmonary vein ostium, and it is capable of directing an ultrasound beam in a desired direction toward an ablation zone.

Preferably the ultrasound beam is transmitted as a continuous wave at an output of approximately 50–60 watts. Typically the input power is 80 watts or less. As the transducer assembly 100 includes a diffraction lens, the natural focal point of the ultrasound beam is given by the formula $$D = \frac{d^2 f}{4c},$$

where d is the transducer diameter, c is the speed of sound and f is the frequency. The focal point is preferably 1–2 cm away from the sensor 108.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art which would occur to persons skilled in the art upon reading the foregoing description.

While this invention has been explained with reference to the structure disclosed herein, it is not confined to the details set forth, and this application is intended to cover any modifications and changes as may come within the scope of the following claims:

The invention claimed is:

1. An apparatus for electrically isolating a cardiac chamber, comprising:
   a guidewire, the guidewire being insertable into a vessel;
   an intravascular catheter having a distal end and a distal tip, said catheter also having a lumen therethrough, said catheter being slidably insertable over said guidewire through said lumen;
   an anchor at said distal tip of said catheter, said anchor being a distal-most component of said catheter and deployable within said vessel and surrounding said guidewire for fixing said catheter near target tissue of an ostium of said vessel; and
   an ultrasound transducer assembly on said catheter and located proximal to said anchor, said ultrasound assembly having a lumen therein for slidably inserting said catheter over said guidewire, said ultrasound assembly comprising a body section having a space therein, said body section shaped as a truncated cone, wherein said body section comprises an air-backing material, said body section also comprising an outer surface at an inclination angle, and said ultrasound assembly also having at least one piezoelectric element made of a ceramic material located within the space of the body section, whereupon in an operational position, said catheter is fixed near said target tissue of said ostium of said vessel by said anchor being deployed within said vessel along said guidewire as said distal-most component of said catheter, and said ultrasound transducer assembly is disposed external to said vessel and said ostium of said vessel and proximal to said anchor, said transducer assembly being spaced a distance away from said target tissue of said ostium of said vessel and said anchor for emitting ultrasound energy that is directed to a circumferential ablation region on said target tissue of said ostium of said vessel, said ultrasound energy emitted along a path substantially avoiding said anchor.

2. The apparatus according to claim 1, further comprising a sensor disposed in said catheter for detecting cardiac electrical activity.

3. The apparatus according to claim 2, further comprising a transmitting antenna disposed in said catheter for transmitting signals from said sensor.

4. The apparatus according to claim 1, wherein said anchor comprises a balloon.

5. The apparatus according to claim 1, wherein a body section of said ultrasound transducer assembly has a proximal cross section and a distal cross section, said proximal cross section being larger than said distal cross section.

6. The apparatus according to claim 5, wherein an inclination angle of said truncated cone is about 20 degrees.

7. The apparatus according to claim 1, wherein said ultrasound transducer assembly comprises an omnidirectional lens that focuses a beam of said ultrasound energy circumferentially on said ablation region.

8. The apparatus according to claim 7, wherein said ultrasound transducer assembly comprises an array of transducer elements, and a control unit for controlling individual ones of said transducer elements to shape said beam.

9. The apparatus according to claim 1, wherein said ultrasound transducer assembly operates at a frequency of between about 3 and 4 MHz.

10. The apparatus according to claim 1, wherein said ultrasound transducer assembly comprises:
 a diffraction grating for directing said ultrasound energy that is output from said ultrasound transducer assembly in a desired direction; and a transducer layer capable of transducing energy delivered thereto at different frequencies, said transducer layer being disposed within said catheter proximate said diffraction grating.

11. The apparatus according to claim 10, wherein said diffraction grating is a thin-film disposed on an external surface of said catheter.

12. The apparatus according to claim 1, wherein said ultrasound transducer assembly has a bandwidth that is between about 50% and about 80% of a primary operating frequency thereof.

13. An apparatus for electrically isolating a cardiac chamber, comprising:
 a guidewire, the guidewire being insertable into a vessel;
 an intravascular catheter having a lumen therethrough, said catheter being slidably insertable over said guidewire through said lumen;
 an anchor at a distal tip of said catheter, said anchor being a distal-most component of said catheter and deployable within said vessel and surrounding said guidewire for fixing said catheter near target tissue of an ostium of said vessel; and
 an ultrasound transducer assembly on said catheter and located proximal to said anchor, said ultrasound assembly having a lumen therein for slidably inserting said catheter over said guidewire, said ultrasound assembly comprising a body section having a space therein, said body section shaped as a truncated cone, wherein said body section comprises an air-backing material, said body section also comprising an outer surface at an inclination angle, and said ultrasound assembly also having at least one piezoelectric element made of a ceramic material located within the space of the body section, whereupon in an operational position, said catheter is fixed near said target tissue of said ostium of said vessel by said anchor being deployed in said vessel along said guidewire as said distal-most component of said catheter, and said ultrasound assembly is disposed external to said vessel and said ostium of said vessel and proximal to said anchor, said transducer assembly being spaced a distance away from said target tissue of said ostium of said vessel and said anchor for emitting ultrasound energy on said target tissue of said ostium of said vessel, said ultrasound energy emitted along a path substantially avoiding said anchor, wherein a body section of said ultrasound transducer assembly has a proximal cross sectional area and a distal cross sectional area, said proximal cross sectional area being larger than said distal cross sectional area, and wherein said ultrasound transducer assembly emits said ultrasound energy as a beam that is focused on an ablation region of said target tissue of said ostium of said vessel that substantially surrounds said ultrasound transducer assembly.

14. The apparatus according to claim 13, further comprising a sensor disposed in said catheter for detecting cardiac electrical activity.

15. The apparatus according to claim 14, further comprising a transmitting antenna disposed in said catheter for transmitting signals from said sensor.

16. The apparatus according to claim 13, wherein said anchor comprises a balloon.

17. The apparatus according to claim 13, wherein an inclination angle of said truncated cone is about 20 degrees.

18. The apparatus according to claim 13, wherein said ultrasound transducer assembly comprises an array of transducer elements, and a control unit for controlling individual ones of said transducer elements to shape said beam.

19. The apparatus according to claim 13, wherein said ultrasound transducer assembly operates at a frequency of between about 3 and 4 MHz.

20. The apparatus according to claim 13, wherein said ultrasound transducer assembly comprises:
 a diffraction grating for directing said ultrasound energy that is output from said ultrasound transducer assembly in a desired direction; and
 a transducer layer capable of transducing energy delivered thereto at different frequencies, said transducer layer being disposed within said catheter proximate said diffraction grating.

21. The apparatus according to claim 20, wherein said diffraction grating is a thin-film disposed on an external surface of said catheter.

22. The apparatus according claim 13, wherein said ultrasound transducer assembly has a bandwidth that is between about 50% and about 80% of a primary operating frequency thereof.

* * * * *